(12) United States Patent
Schiffler

(10) Patent No.: US 8,587,784 B2
(45) Date of Patent: Nov. 19, 2013

(54) OPTICAL ANALYSIS DEVICE

(75) Inventor: Ingo Schiffler, Freiburg (DE)

(73) Assignee: Sick AG, Waldkirch (DE)

( * ) Notice: Subject to any disclaimer, the term of this patent is extended or adjusted under 35 U.S.C. 154(b) by 238 days.

(21) Appl. No.: 13/227,167

(22) Filed: Sep. 7, 2011

(65) Prior Publication Data

US 2012/0055238 A1    Mar. 8, 2012

(30) Foreign Application Priority Data

Sep. 8, 2010   (EP) .................................... 10009348

(51) Int. Cl.
*G01N 21/00*   (2006.01)

(52) U.S. Cl.
USPC ....................................................... 356/436

(58) Field of Classification Search
USPC ......... 356/213, 436; 73/61.41, 31.05; 385/12, 385/147
See application file for complete search history.

(56) References Cited

U.S. PATENT DOCUMENTS 5,969,811 A * 10/1999 Waller et al. ................... 356/246
2001/0010747 A1 * 8/2001 Dourdeville et al. .......... 385/147

FOREIGN PATENT DOCUMENTS

| DE | 38 39 348 A1 | 6/1989 |
| DE | 40 18 844 A1 | 1/1991 |
| DE | 198 43 553 A1 | 4/2000 |
| DE | 10 2004 018 534 B4 | 11/2005 |
| DE | 10 2005 025 181 A1 | 12/2006 |

OTHER PUBLICATIONS

European Search Report, Application No. EP 10 00 9348, mailed on Jun. 8, 2011.

* cited by examiner

*Primary Examiner* — Tarifur Chowdhury
*Assistant Examiner* — Abdullahi Nur
(74) *Attorney, Agent, or Firm* — Nath, Goldberg & Meyer; Jerald L. Meyer

(57) ABSTRACT

The invention relates to an optical analysis device for analyzing a medium in a measurement volume, comprising a housing having an opening, a flange for holding the housing in a reception opening of the measurement volume and an optical analysis unit in the housing. In accordance with the invention, a fastening stub provided at the housing and including the opening is provided for fastening the housing in the flange, with the fastening stub having an outer geometry which is matched to the inner geometry of the flange such that it can be displaced in the flange in the direction of the measurement volume and away from it. A clip is provided with which the flange and the fastening stub can be connected to one another in shape-matched and/or force-transmitting manner in different positions of the fastening stub in the flange.

11 Claims, 6 Drawing Sheets

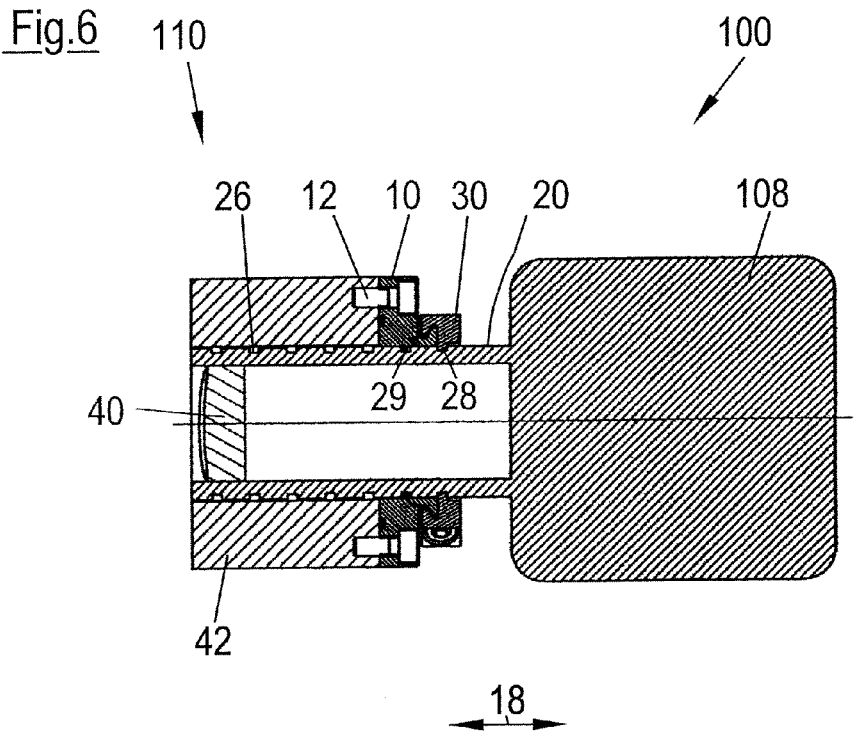
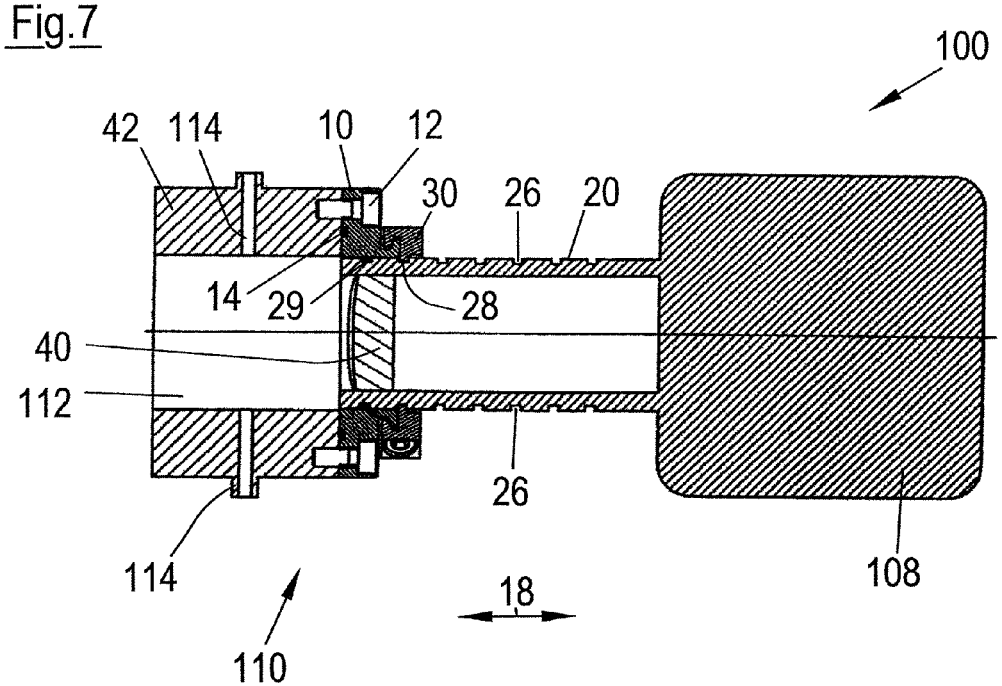

OPTICAL ANALYSIS DEVICE

The invention relates to an optical analysis device for analyzing a medium in a measurement volume having the features of the preamble of claim 1. It includes a housing having an opening, a flange for holding the housing in a reception opening of the measurement volume and an optical analysis unit.

Such analysis devices serve, for example, for determining the concentration of gases or of dust particles or sooty particles in industrial flue gas stacks. For this purpose, a transmission light measurement can be carried out, on the one hand, in which a transmitted light beam is led through a measurement volume—for example transversely through an exhaust gas passage—wherein that portion of the transmitted light is measured by means of an associated light receiver which only acts on the light receiver in an attenuated manner since a portion of the transmitted light is absorbed by particles or molecules in the measurement volume. The concentration in the measurement volume can be determined from the measured attenuation of the transmitted light. Such a transmission light measurement can also be carried out, for example, using a reflector so that the light transmitter and the light receiver can be arranged on the same side of the measuring volume and only the light reflector is provided at the other side.

On the other hand, scattered light measurements can be carried out in which the transmitted light is detected which is scattered at the particles within the measurement volume. Such an optical particle concentration measurement device is described in DE 10 2005 025 181 A1.

Such analysis devices are used for observing or for measurements of a medium, for example of a gas or of a liquid, in the measurement volume. The term "measurement volume" is used here for the space in which the medium to be observed or to be measured is located or moved respectively. It can in this respect therefore, for example, be a corresponding container or a passage or a pipe.

In particular gas measurement devices which are coupled to plants via flanges often include a flushing arrangement which serves for the keeping pure of optical boundary surfaces which are located, for example, in the form of windows between the measurement volume and the gas measurement device. On the other hand, the contact between the measurement medium and the device can be avoided by a flushing arrangement when the measurement medium is, for example, a corrosive gas. An optical system having a flushing of an inspection window is described in DE 10 2004 018 534 B4.

Devices having a flushing arrangement, however, have very large dead volumes in the region of the coupling of the measurement device to the measurement volume. Such devices must as a rule also be flushed on the use of clean (that is, for example, low-dust and non-corrosive) applications so that the measured value of the particle concentration is not impaired via other concentrations or a different time behavior within the dead volumes.

On the other hand, devices without a flushing arrangement are as a rule not suitable for dirty media and additionally in turn have a dead volume too small for other applications.

It is the object of the present invention to provide an optical analysis device with which a flexible setting of the process connector to the measurement volume is possible.

This object is satisfied by an optical analysis device having the features of claim 1. Dependent claims are directed to preferred embodiments.

The device in accordance with the invention includes a flange for holding the housing in a reception opening of the measurement volume. The housing with the measurement volume is therefore not only simply screwed or, for example, fixedly welded to the measurement volume. Instead, a flange is provided to hold the housing with the measurement structure.

A fastening stub with which the housing can be fastened to the flange is provided at the housing itself in accordance with the invention, with the outer geometry of the fastening stub being matched to the inner geometry of the flange such that the fastening stub can be displaced in the direction of the measurement volume and away from it. The fastening stub can have a seal which seals the outer side of the fastening stub with respect to the inner side of the flange. In accordance with the invention, a clip is additionally provided with which the flange and the fastening stub can be connected to one another in shape-matched or force-transmitting manner in different positions of the fastening stub in the flange.

An optical analysis unit is located in the housing for the optical analysis of the medium in the measurement volume through the opening of the housing. It can in this respect, for example, be a transmission element in the housing for transmitting a measuring light beam through the opening into the measurement volume and a reception element in the housing for receiving scattered or transmitted light from the measurement volume.

In an optical analysis unit, the measurement arrangement contained in the housing is as a rule terminated by an inspection window so that the measurement arrangement (which comprises a transmission element and a reception element in the example described) is terminated with respect to the measurement volume in operation.

An optical analysis device in accordance with the invention makes it possible that the housing with the optical analysis unit can be displaced in the flange for holding the housing in a reception opening of the measurement volume. Depending on the configuration and size of the flange, a matching depth setting of the housing can therefore be set in the reception opening of the measurement volume. The analysis device in accordance with the invention is particularly flexible in this respect. A flush process connector with a small dead volume or with no dead volume at all can be set, for example, in which an inspection window of the analysis device is flush with the wall of the measurement volume. Such a setting is in particular suitable for clean, non-corrosive media to be examined at moderate temperatures at which no flushing of the process connector is necessary. With an offset process connector in which a specific spacing is desired between the optical analysis unit and the measurement volume and in which a flushing arrangement is required to this extent, a larger spacing of the optical analysis unit from the measurement volume can be set. Optionally, a dead volume can also be deliberately produced in this manner which is available for a flushing arrangement.

A particular embodiment of the analysis device in accordance with the invention includes a fastening stub which is tubular. An optics mount can in particular be provided in which a light directing element is provided which leads the light of the transmission element into the measurement volume or out of the measurement volume to the reception element or an inspection window is provided.

Such a tubular fastening stub can be displaced and fastened in a simple manner within the flange. For example, the flange can have at its outer periphery a radially outwardly facing prolongation at which a prolongation can engage which faces radially inwardly and is provided at the clip which engages around the flange.

The clip can hold the fastening stub in a force-transmitting manner via a clamping connection, for example.

To achieve a shape-matched connection, the fastening stub can have a plurality of first engagement elements at its outer periphery and the clip can have at least one corresponding second engagement element at its inner periphery. Depending on which of the first engagement elements of the fastening stub the at least one second engagement element cooperates with, different setting depths of the fastening stub in the flange can be realized.

In a preferred embodiment, the first engagement elements are designed as grooves and the at least one second engagement element of the clip as a corresponding tongue. A groove-and-tongue connection is particularly stable to ensure a corresponding shape matching.

In addition, seals can moreover be provided in a simple manner at a suitable point in individual grooves of the fastening stub to seal the fastening stub against the flange.

An embodiment is particularly advantageous in which the flange can be releasably connected to the measurement volume. In this manner, different flanges can be fastened in a simple manner to the measurement volume to make use of different fastening stubs and analysis devices.

A corresponding flange can be designed in a multipart manner to be able to set different flange lengths.

An optical analysis device in accordance with the invention can also be used with a measurement volume in which a reception stub projecting from its wall is present to whose end remote from the measurement volume the flange of the optical analysis device can be fastened. The fastening stub of the optical analysis device can be pushed into the reception stub in a desired depth in order thus to be able to realize different dead volumes.

An optical analysis device in accordance with the invention can advantageously be used for measuring and observing gas. A use of liquids is equally possible.

The optical analysis device in accordance with the invention is in particular suitable for the measurement of concentrations. For example, the scattering of light in the measurement volume can be measured to determine the particle concentration. Such a measurement arrangement is suitable, for example, for determining the dust portion or sooty portion in the flue gas of a stack. For this purpose, the optical analysis device is flanged to a side opening of the stack, with the interior of the stack representing the measurement volume.

On a corresponding design of the optical analysis unit, the optical analysis device in accordance with the invention can, on the other hand, also be used, for example, for determining the composition of a medium in the measurement volume. The optical analysis unit in the housing of the optical analysis device in accordance with the invention can thus include, for example, a spectroscopic evaluation device for the reflected light received from the measurement volume.

The invention is, however, not restricted to such optical analysis devices.

The invention will be described in detail with reference to the enclosed Figures which show embodiments of an optical analysis device in accordance with the invention.

FIG. 6 shows a part sectional view of another embodiment of an analysis device in accordance with the invention in a use with a specially designed measurement volume with a connector stub; and FIG. 7 shows the arrangement of FIG. 6 in another state of use;

Figure 2:
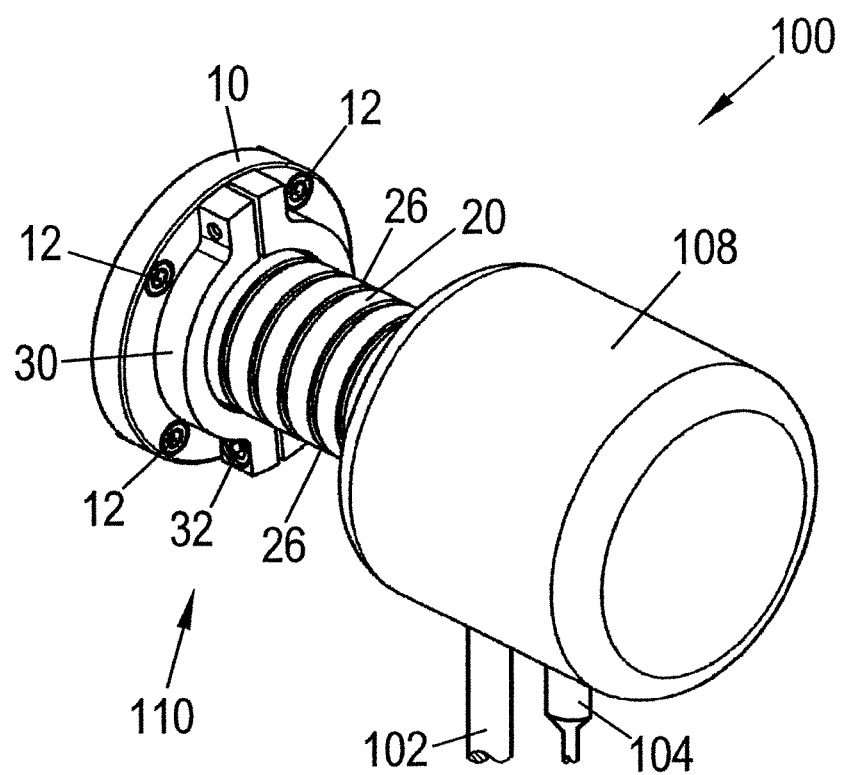
FIG. 2 shows an oblique plan view of an analysis device in accordance with the invention.

The optical analysis device 100 shown in FIG. 2 has a housing 108. There are located therein, for example, in a manner known per se a transmission element and a reception element respectively for transmitting and receiving light (visible light, ultraviolet light or infrared light) which form an optical analysis unit. The light beam transmitted by the transmission element is transmitted by a fastening stub 26 in the direction of a measurement volume within which a medium is located whose concentration or composition is to be measured. The measurement volume can, for example, be a passage through which the medium flows or a container in which the medium is located. The optical analysis device 100 is for this purpose screwed with a flange 10 using the fastening screws 12 at a reception opening of the measurement volume not shown here. Stubs 102, 104 through which electrical feed lines, control lines and data lines are introduced into the housing 108 in a manner known per se are located at the optical analysis device 100.

Figure 1:
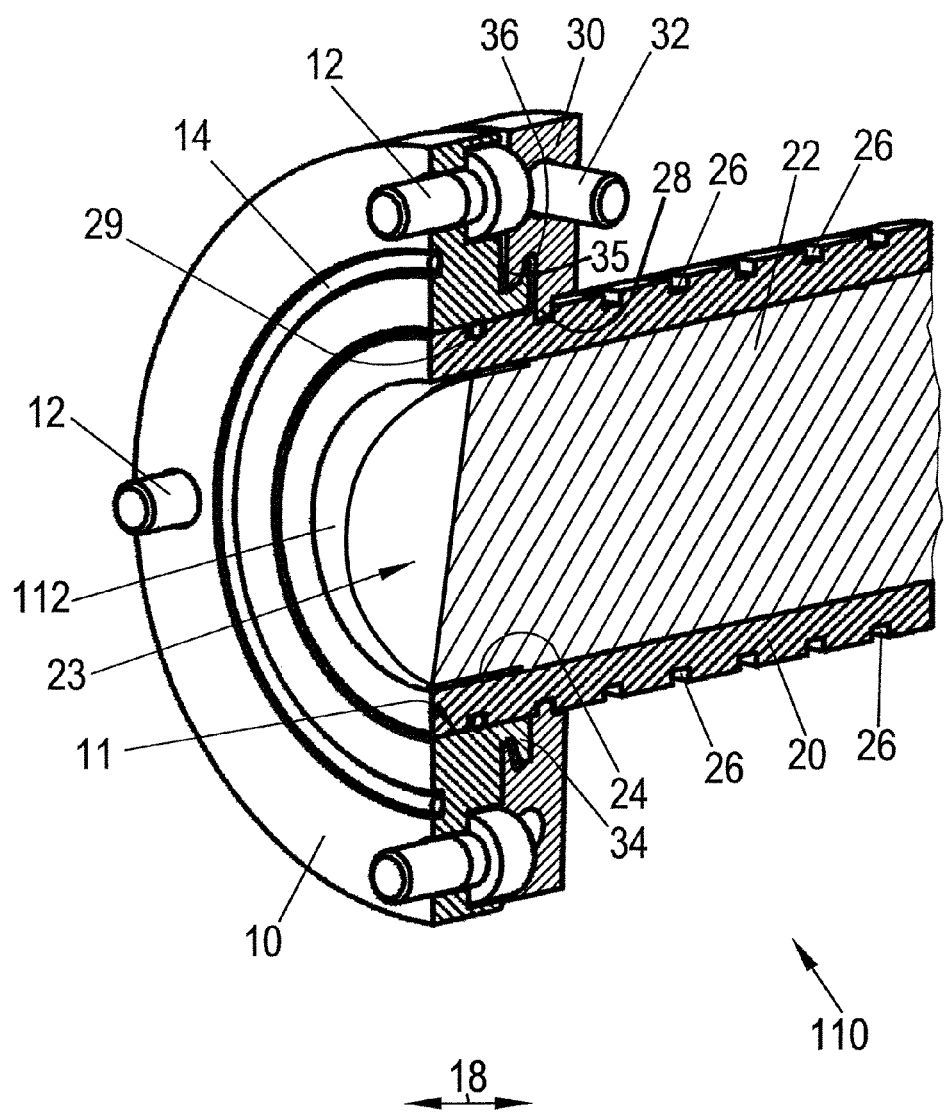
FIG. 1 shows a part sectional view of the process connector of an analysis device in accordance with the invention.

The embodiment of the connector part 110 of the analysis device 100 to the measurement volume is shown in detail in FIG. 1.

The flange 10, with whose aid the connector part can be fastened to the measurement volume, not shown, is located at the left side of FIG. 1. For this purpose, fastening screws 12 are provided which can be screwed into corresponding thread openings in the wall of the measurement volume. An O ring seal 14 is provided in a corresponding groove of the flange 10 for sealing the flange 10 with respect to the wall of the measurement volume. The flange 10 has an inner opening 11 into which a fastening stub 20 can be pushed which—as is visible in FIG. 2—projects out of the optical analysis device 100 on a side of the housing 108. An opening 21 which faces in the direction of the measurement volume in operation, is located at the end of the fastening stub remote from the housing. The fastening stub 20 is fastened in a manner still to be described by a clip 30 to the flange 10. It is sealed toward the inner opening 11 of the flange 10 via an O ring seal 29.

An optical light directing element 22, for example an optical fiber, is guided into the fastening stub 20 and can be fastened (for example adhesively bonded) and optionally sealed in a manner known per se in the fastening stub 20 via suitable fastening means 24. The fastening stub 20 can include an optics mount for this purpose, for example.

The optical directing element 22 serves for guiding the light of the transmission element from the optical analysis device 100 in the direction of the measurement volume to be fastened on the left side of FIG. 1. The boundary surface of the optical directing element 22 in the direction of the measurement volume is designated by reference numeral 23.

Alternatively, instead of the optical directing element, an optical inspection window or a lens can be used and optionally sealed. To avoid reflections, the optical boundary surface of the optical directing element 22 or of the optical inspection window can be set obliquely toward the measurement volume.

The housing 108, not shown in this Figure, adjoins on the right side of FIG. 1.

A plurality of grooves 26 are located at a defined interval at the outer periphery of the fastening stub 20. Tongues 28 provided at the inner periphery of the clip 30 can engage into the grooves 26 to enable a shape match. The grooves 26 can also be arranged such that at least one thereof serves for the reception of an O ring 29 which seals the fastening stub 20 toward the flange 10.

The clip 30 additionally has a peripheral prolongation 35 at its inner periphery which delineates a cut-out 36 which includes the peripheral outwardly facing prolongation 34 of the flange 10.

If the clip 30 is not attached, the fastening stub 20 can be pushed by the flange in the direction 18.

A flexible setting is possible using the arrangement in accordance with the invention. The flange 10 can be fastened to a measurement volume with the help of the fastening stub 12 so that the opening 11 corresponds with a corresponding reception opening in the measurement volume. The flange is in this respect sealed with respect to the wall of the measurement volume by the O ring seal 14. The fastening stub 20 with the optical directing element 22 can be pushed into the flange. An O ring seal 29 in one of the grooves 26 in this respect serves for the sealing of the outer surface of the fastening stub 20 toward the inner surface 11 of the flange 10.

The fastening stub 20 is fastened to the flange 10 by the clip 30. For this purpose, the clip is placed around the prolongation 34 and the tongue 28 is brought into engagement with one of the grooves 26. The clip 30 is held in shape-matched manner at the fastening stub 20 by tightening the screws 32 (FIG. 2).

A use is shown in FIG. 1 in which a dead volume 112 is provided which is as small as possible.

Figure 3:
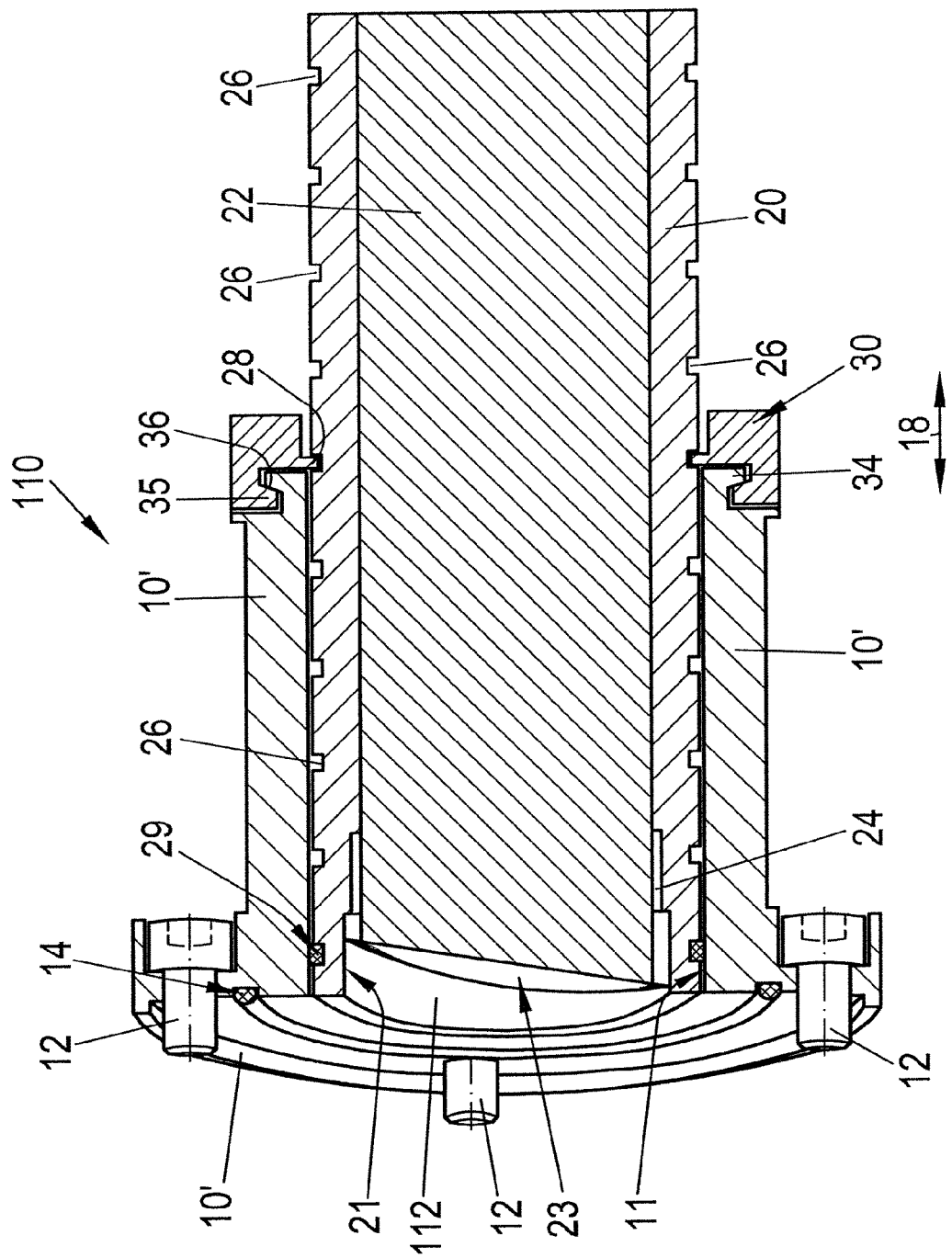
FIG. 3 shows another embodiment with a longer flange in a first manner of use.

FIG. 3 shows a further embodiment with a flange 10 longer in the axial direction. The dead volume 112 arising in the embodiment of FIG. 3 approximately corresponds in size to the dead volume of the embodiment of FIG. 1. However, due to the longer flange design, a more secure connection is possible between the fastening stub 20 which is secured more reliably against tilting because it can be supported over a larger area at the inner surface 11 of the flange 10. The remaining function corresponds to the mode of operation described with reference to the embodiment of FIG. 1. Elements which are the same or similar are therefore designated by the same reference numerals.

Figure 4:
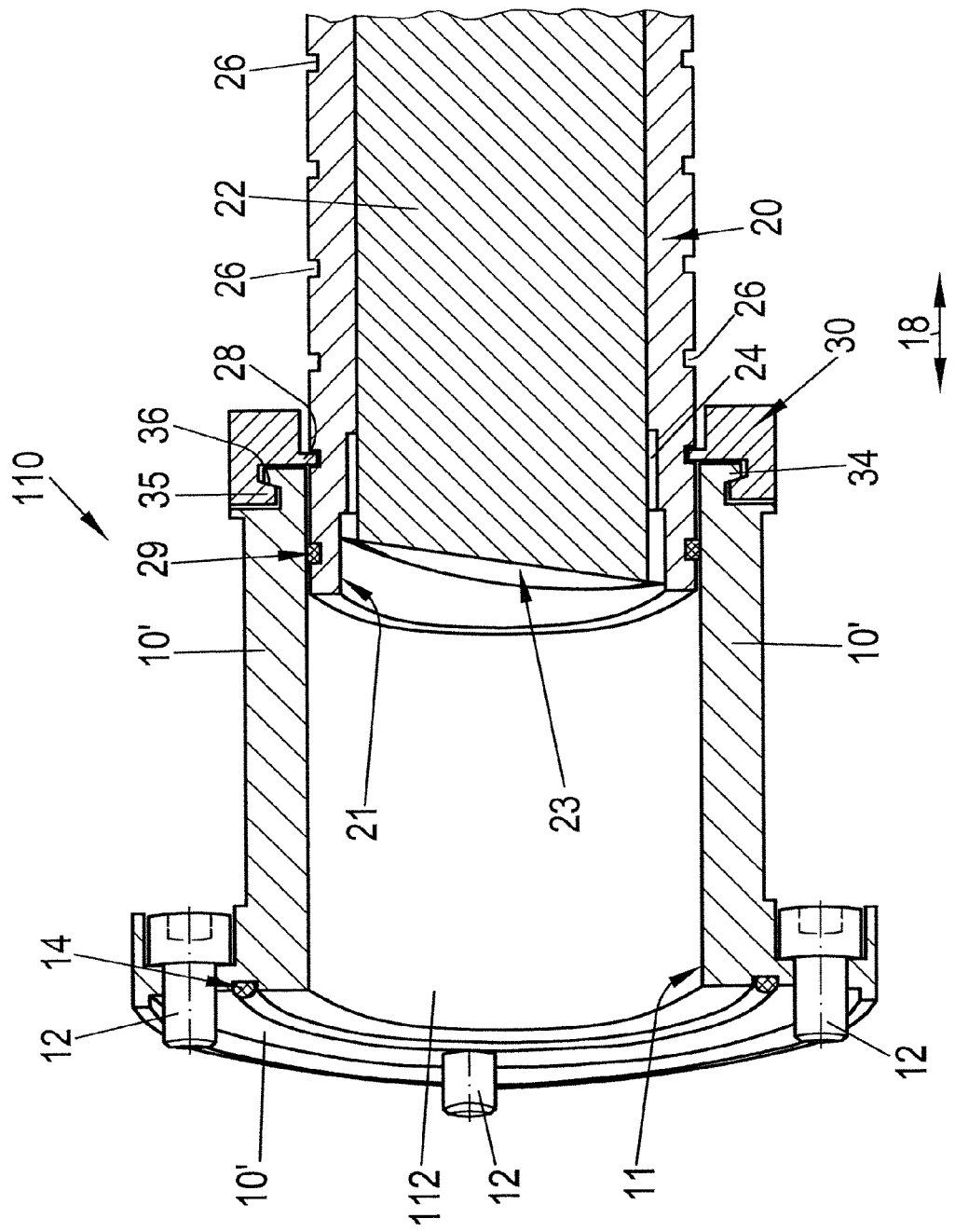
FIG. 4 shows the embodiment of FIG. 3 in another manner of use.

FIG. 4 shows the same embodiment in a different mode of use. The fastening stub 20 has here not been pushed as far in the flange 10' and then fastened in the described manner with the clip 30 while using one of the grooves 26. A larger dead volume 112 thus arises which is desirable in some applications (for example when using corrosive gas in the measurement volume).

Figure 5:
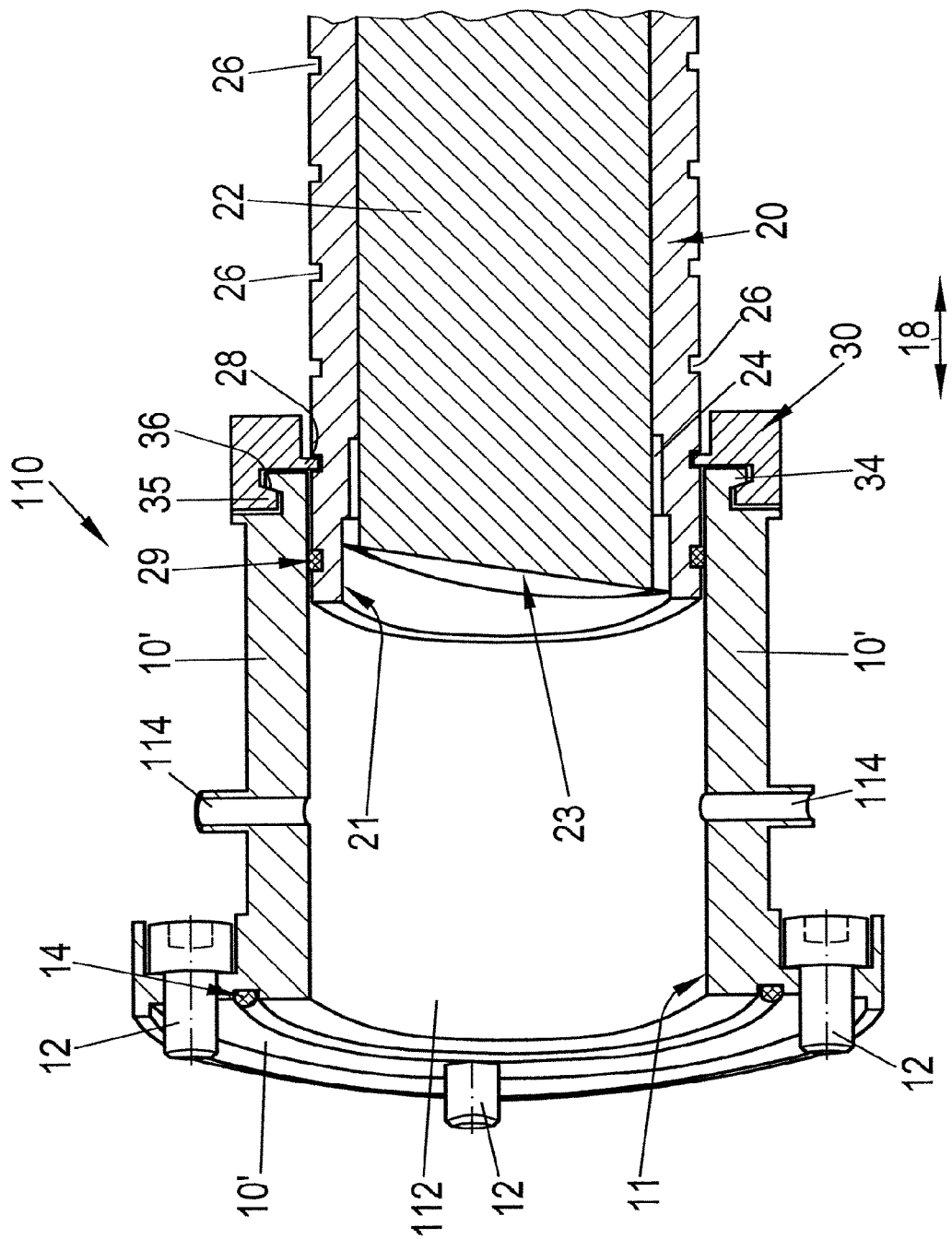
FIG. 5 shows a use with a flushing device.

In particular in such an embodiment, a flushing arrangement can also be provided which flushes the dead volume 112 and so provides defined conditions. For this purpose, openings and connectors 114 for the introduction of flushing gas can be provided in the flange 10', for example, FIG. 5 shows such an arrangement by way of example.

Different connector geometries can easily be realized by use of different flanges.

FIGS. 6 and 7 show an embodiment similar to that of FIG. 1 in a different state of use. The optical analysis device 100 in accordance with the invention is in particular used here with a measurement volume whose wall has a reception stub 42 which is directed away from the measurement volume.

The reception stub adjoins the wall of the measurement volume, not shown, on the left side of the reception stub 42. The arrangement of the flange 10, of the clip 30 and of the fastening stub 20 corresponds to the embodiment of FIG. 1.

Differing from the embodiments shown in FIGS. 1 and 3 to 5, no optical directing element 22 is provided in the optical analysis device 100 here, but rather an inspection window 40 of transparent material through which the light of the optical analysis unit arranged in the housing 108 and comprising the transmission element and the reception element passes. The inspection window 40 can optionally also satisfy a lens function.

The fastening stub 20 of the optical analysis device 100 can be pushed into the reception stub 42.

FIG. 6 shows a use in which the fastening stub 20 is pushed far into the reception stub 42 to produce a small dead volume. The tongue 28 of the clip 30 here engages into a groove 26 of the fastening stub 20 which is arranged close to the housing 108.

FIG. 7 shows a use in which the fastening stub 20 is pushed less far into the reception stub 42 of the measurement volume. The tongue 28 here engages into a groove 26 which is arranged close to the end of the fastening stub 20. A larger dead volume 112 arises in this manner.

FIG. 7 shows, in contrast to FIG. 6, a section through a plane in which flushing gas connectors 114 for flushing the dead volume 112 can be recognized. With a fastening stub 20 pushed further into the receiving stub 42 (as shown in FIG. 6), the flushing gas connectors 114 are not used since also no such large dead volume 112 is present as in the use in accordance with FIG. 7.

An embodiment not shown has a flange, for example, which is designed in a multipart manner, in particular containing a plurality of rings which can be coupled to one another. Differently long flange geometries can thus be set.

When using a corresponding optics or light director for guiding the measuring light from the optical analysis unit to the measurement volume, it is also possible, differently from the embodiments shown, that the fastening stub is not straight-line and/or is at least partly flexible.

The optical analysis device in accordance with the invention therefore allows, on the use of suitably dimensioned flanges, a very flexible setting of the dead volume between the optical arrangement and the measurement volume. A use with different connector geometries of the measurement volume is easily possible.

REFERENCE NUMERAL LIST 10, 10' flange
11 inner flange surface
12 fastening screw
14 O ring seal
18 pushing direction
20 fastening stub
21 opening of the fastening stub
22 optical directing element
23 optical boundary surface
24 fastening means
26 groove
28 tongue
29 seal
30 clip
32 clip screw
34 prolongation
35 prolongation
36 cut-out
40 inspection window
42 reception stub
100 optical analysis device
102, 104 connectors
108 housing
110 process connector piece
112 dead volume
114 flushing gas connector

The invention claimed is:

1. An optical analysis device (100) for analyzing a medium in the measurement volume, comprising
a housing (108) having an opening (21);
a flange (10, 10') for holding the housing (108) in a reception opening of the measurement volume; and
an optical analysis unit in the housing (108) for the optical analysis of a medium in the measurement volume through the opening (21), further comprising:
a fastening stub (20) provided at the housing and including the opening (21) for fastening the housing (108) in the flange (10, 10'), with the fastening stub (20) having an outer geometry which is matched to the inner geometry of the flange (10, 10') such that it can be displaced in the flange (10, 10') in the direction of the measurement volume and away from it; and a clip (30) with which the flange (10, 10') and the fastening stub (20) can be connected to one another in shape-matched and/or force-transmitting manner in different positions of the fastening stub (20) in the flange (10, 10'), wherein the flange (10, 10') has a radially outwardly facing prolongation (34) at its outer periphery and the clip (30) has a radially inwardly facing prolongation (35) such that the inwardly facing prolongation (35) of the clip (30) can engage around the outwardly facing prolongation (35) of the flange.

2. An optical analysis device in accordance with claim 1, wherein the optical analysis unit includes at least one transmission element in the housing (108) for transmitting a measuring light beam through the opening (21) into the measurement volume and at least one reception element in the housing (108) for receiving scattered light or transmitted light from the measurement volume.

3. An optical analysis device in accordance with claim 1, wherein the fastening stub (20) is tubular.

4. An optical analysis device in accordance with claim 1, wherein the fastening stub (20) has a plurality of first engagement elements (26) at its outer periphery and the clip (30) has at least one corresponding second engagement element (28) at its inner periphery, with the first engagement elements (26) being arranged such that the fastening stub (20) projects differently far into the reception opening of the measurement volume depending on which of the first engagement elements (26) of the fastening stub (20) the at least one second engagement element (28) cooperates with.

5. An optical analysis device in accordance with claim 4, wherein the first engagement elements include grooves (26) and the at least one second engagement element includes a corresponding tongue (28).

6. An optical analysis device in accordance with claim 1, wherein the flange (10, 10') can be releasably connected to the measurement volume.

7. An optical analysis device in accordance with claim 1, wherein the flange is designed in a multipart manner.

8. An optical analysis device in accordance with claim 1, wherein the fastening stub (20) includes a seal (29) which seals the outer side of the fastening stub (20) with respect to the inner side of the flange (10, 10').

9. An optical analysis device in accordance with claim 1, wherein it is a particle concentration measurement device for measuring a particle concentration in the measurement volume.

10. An optical analysis device in accordance with claim 1, wherein it is a device for the concentration determination and/or composition determination of a gas.

11. An optical analysis device in accordance with claim 1, wherein it is a device for the concentration determination and/or composition determination of a liquid.

* * * * *